United States Patent

Wang

Patent Number: 6,015,769

Date of Patent: *Jan. 18, 2000

[54] VINYL ACETATE CATALYST COMPRISING METALLIC PALLADIUM, GOLD AND COPPER SUPPORTED ON A CARRIER AND PREPARED WITH POTASSIUM AURATE

[75] Inventor: Tao Wang, Corpus Christi, Tex.

[73] Assignee: Celanese International Corporation, Dallas, Tex.

[*] Notice: This patent is subject to a terminal disclaimer.

[21] Appl. No.: 09/088,980

[22] Filed: Jun. 2, 1998

[51] Int. Cl.[7] .............................. B01J 23/72; B01J 23/00; B01J 23/59; B01J 23/42

[52] U.S. Cl. ..................... 502/331; 502/325; 502/330; 502/339

[58] Field of Search .................... 502/325, 330, 502/331, 339

[56] References Cited

U.S. PATENT DOCUMENTS

| | | | |
|---|---|---|---|
| 4,087,622 | 5/1978 | Nakamura et al. | 502/170 |
| 4,119,567 | 10/1978 | Bartsch | 502/331 |
| 4,764,498 | 8/1988 | Wissner et al. | 502/251 |
| 5,179,057 | 1/1993 | Bartley | 502/170 |
| 5,314,858 | 5/1994 | Colling | 502/330 |
| 5,332,710 | 7/1994 | Nicolau et al. | 502/243 |
| 5,347,046 | 9/1994 | White et al. | 560/245 |
| 5,693,586 | 12/1997 | Nicolau et al. | 502/330 |
| 5,700,753 | 12/1997 | Wang et al. | 502/330 |
| 5,731,457 | 3/1998 | Nicolau et al. | 560/245 |

FOREIGN PATENT DOCUMENTS 1188777  4/1967  United Kingdom .

OTHER PUBLICATIONS

Journal of The American Chemical Society, 1927, vol. 49, pp. 1221–1226, May 1927.

*Primary Examiner*—Mark L. Bell
*Assistant Examiner*—Patricia L. Hailey
*Attorney, Agent, or Firm*—M. Susan Spiering

[57] ABSTRACT

A catalyst for the production of vinyl acetate by reaction of ethylene, oxygen and acetic acid comprising a porous support on the porous surfaces of which is deposited catalytically effective amounts of metallic palladium, gold and copper, said catalyst having been prepared by steps comprising impregnating said support, the porous surfaces of which contain catalytically effective amounts of prereduced metallic palladium and copper, with a solution of potassium aurate, and reducing the potassium aurate to a catalytically effective amount of metallic gold. Alternatively, the support may first be contacted with gold followed by contact with palladium/copper complexes. A still further alternative includes use of sodium free reagents.

26 Claims, No Drawings

VINYL ACETATE CATALYST COMPRISING METALLIC PALLADIUM, GOLD AND COPPER SUPPORTED ON A CARRIER AND PREPARED WITH POTASSIUM AURATE

BACKGROUND OF THE INVENTION

1. Field of the Invention

This invention relates to new and improved catalysts for the production of vinyl acetate by reaction of ethylene, oxygen and acetic acid.

2. Background Information Including Description of Related Art

It is known to produce vinyl acetate by reaction of ethylene, oxygen and acetic acid using a catalyst consisting of metallic palladium, gold and copper supported on a carrier. While the process utilizing such a catalyst is capable of producing vinyl acetate at fair levels of productivity, any expedient capable of achieving even greater productivity involving use of a catalyst which in some respects is easier to produce than those employed heretofore, is obviously advantageous.

The catalysts comprising metallic palladium, gold and copper known prior to this invention are conventionally prepared by a process including the steps of impregnating a porous support with a single aqueous solution or separate solutions of water-soluble salts of the palladium, gold, and copper; reacting the impregnated water-soluble salts with an appropriate alkaline compound e.g., sodium hydroxide, to "fix" the metallic elements as water-insoluble compounds, e.g. the hydroxides; and reducing the water insoluble compounds, e.g., with ethylene or hydrazine, to convert the metallic elements to free metallic form. This type of process has the disadvantage of requiring several steps, sometimes including at least two fixing steps.

The following references may be considered material to the invention claimed herein. U.S. Pat. No. 5,332,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution to precipitate such compounds, and subsequently reducing the compounds to free metallic form.

U.S. Pat. No. 5,347,046, issued Sep. 13, 1994 to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

British Patent No. 1,188,777, published Apr. 22, 1970 discloses a process for the simultaneous production of an unsaturated carboxylic acid ester, e.g. vinyl acetate, by reaction of an olefin, carboxylic acid, and oxygen, and the corresponding carboxylic acid, e.g., acetic acid, from its aldehyde, using a single supported catalyst containing a palladium compound, e.g. an oxide or salt, with one or more compounds of any of various metals, e.g. metallic gold or a gold compound such as potassium aurate.

U.S. Pat. No. 5,700,753 discloses vinyl acetate (VA) catalyst prepared by adding organometallic gold complexes to prereduced palladium catalyst prepared from $Na_2PdCl_4$. The organometallic gold compound does not require a fixing procedure.

U.S. Pat. No. 5,731,457 describes a VA catalyst prepared with non-halogen containing copper compound.

SUMMARY OF THE INVENTION

In accordance with this invention, a catalyst is provided useful for the production of vinyl acetate by reaction of ethylene, oxygen and acetic acid with low carbon dioxide selectivity, said catalyst being prepared by steps comprising impregnating a porous support, the porous surfaces of which contain catalytically effective amounts of prereduced metallic palladium and copper, with a solution of potassium aurate ($KAuO_2$) and reducing the potassium aurate to a catalytically effective amount of metallic gold. Alternatively, prereduced metallic gold, via use of potassium aurate, may first be impregnated onto the support, followed by the impregnation, fixing, and reduction of Pd and Cu complexes onto the support. The use of such catalyst often results in lower carbon dioxide and heavy ends selectivities, which are usually accompanied by a higher vinyl acetate productivity, than when various conventional catalysts comprising metallic palladium and gold are employed.

As a further alternative, the catalyst may be prepared employing sodium free reagents. For example, the potassium salts of the reagents disclosed herein may be employed.

DETAILED DESCRIPTION OF THE INVENTION

In accordance with this invention, a catalyst is provided useful for the production of vinyl acetate by reaction of ethylene, oxygen and acetic acid with low carbon dioxide selectivity, said catalyst comprising a porous support on to which is deposited catalytically effective amounts of metallic palladium, gold, and copper, said catalyst prepared by the steps comprising (1) impregnating the support with catalytically effective amounts of water soluble palladium and copper solutions, followed by fixing and reduction of the Pd and Cu to their metallic form; (2) contacting the prereduced Pd/Cu catalyst with a solution of potassium aurate, and reducing the potassium aurate to a catalytically effective amount of metallic gold.

Alternatively, the support may (1) first be contacted with a solution of potassium aurate, reducing the potassium aurate to a catalytically effective amount of metallic gold, and (2) contacting with catalytically effective amounts of water soluble palladium and copper solutions, followed by reduction of the Pd and Cu to their metallic form.

The use of the inventive catalyst often results in lower carbon dioxide selectivity, which is usually accompanied by a higher vinyl acetate productivity, than when various conventional catalysts comprising metallic palladium and gold are employed.

The catalyst support material is composed of particles having any of various regular or irregular shapes, such as spheres, tablets, cylinders, rings, stars, or other shapes, and may have dimensions such as diameter, length or width of about 1 to about 10 mm., preferably about 3 to 9 mm. Spheres having a diameter of about 4 to about 8 mm. are preferred. The support material may be composed of any suitable porous substance, e.g., silica, alumina, silica-alumina, titania, zirconia, silicates, aluminosilicates, titanates, spinel, silicon carbide, carbon, and the like.

The support material may have a density in the range, for example, of about 0.3 to about 1.2 g/ml, an absorptivity in the range, for example, of about 0.3 to 1.5 g $H_2O$/g support, a surface area within the range, for example, of about 10 to about 350, preferably about 100 to about 200 m²/g, an average pore size in the range, for example, of about 50 to about 2000 angstroms, and a pore volume in the range, for example, of about 0.1 to about 2, preferably about 0.4 to about 1.2 ml/g.

In the preparation of the catalyst used in the process of this invention, the support material is first treated to deposit catalytic amounts of palladium and copper on the porous surfaces of the support particles. Any of various methods for accomplishing this purpose may be used, all of which involve the impregnation of the support with an aqueous solution of water-soluble compounds, e.g. salts, of palladium and copper. Palladium(II) chloride, sodium palladium (II) chloride (i.e., sodium tetrachloropalladium(II), $Na_2PdCl_4$), potassium palladium(II) chloride, palladium(II) nitrate or palladium(II) sulfate are examples of suitable water-soluble palladium compounds, while, for example, cupric chloride (anhydrous or dihydrate), cupric nitrate trihydrate, cupric acetate (anhydrous or monohydrate), cupric sulfate, or cupric bromide and the like, may be used as the water-soluble copper compound. Sodium tetrachloropalladium(II) and cupric chloride are the preferred salts for impregnation because of their good water solubility. The impregnation can be accomplished by the "incipient wetness" method wherein an amount of water-soluble metal compound solution used for the impregnation is from about 95 to about 100 percent of the absorptive capacity of the support material. The concentration of the solution is such that the amount of elemental palladium and copper in the solution absorbed on the support is equal to a desired predetermined amount. The impregnation is such as to provide, for example, about 1 to about 10 grams of elemental palladium, and, for example, about 0.3 to about 5.0 grams, preferably about 0.5 to about 3.0 grams of elemental copper, per liter of finished catalyst.

After the impregnation of the support with an aqueous solution of water-soluble compounds of palladium and copper, the compounds are "fixed", i.e., precipitated, as water-insoluble compounds such as the hydroxides, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkali metal in the alkaline compound should be in an amount of, for example, about 1 to about 2, preferably about 1.1 to about 1.8 times the amount necessary to react with the catalytically active cations present in the water-soluble salt. The fixing of the palladium and copper may be done by the incipient wetness method wherein the impregnated support is dried, e.g., at a temperature of 150° C. for one hour, contacted with an amount of solution of the alkaline material equal to about 95–100% of the pore volume of the support, and allowed to stand for a period of about ½ to about 16 hours; or the roto-immersion method wherein the impregnated support without drying is immersed in a solution of the alkaline material and is rotated and/or tumbled during at least the initial period of precipitation such that a thin band of the precipitated water-insoluble compounds is formed at or near the surface of the support particles. The rotation and tumbling may be carried out, for example, at about 1 to about 10 rpm for a period, e.g., of at least about 0.5 hour, preferably about 0.5 to about 4 hours. The contemplated roto-immersion method is disclosed in U.S. Pat. No. 5,332,710, the entire disclosure of which is incorporated herein by reference.

The fixed palladium and copper compounds may then be reduced, for example, in the vapor phase with ethylene, e.g., 5% in nitrogen at 150° C. for 5 hours, after first washing the catalyst containing the fixed compounds until it is free of anions such as halide, and drying, e.g., at 150° C. overnight under constant $N_2$ purge, or such reduction may be accomplished in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed palladium and copper compounds present on the support may be employed as conventional in the art. The reduction of the fixed compounds results mainly in the formation of the free metals, although a minor amount of metal oxides may also be present.

While the impregnation, fixing and reduction of the palladium and copper have been described as being carried out simultaneously, these three steps can in fact be carried out for the palladium and copper separately.

After the support containing palladium and copper in free metallic form is prepared by any of the foregoing methods, it is impregnated with an aqueous solution of potassium aurate, preferably by incipient wetness. The catalyst is then dried such that the catalyst contains potassium aurate in an amount sufficient to provide, for example, about 0.5 to about 10 grams of elemental gold per liter of finished catalyst, with the amount of gold being from about 10 to about 125 wt. % based on the weight of palladium present. The potassium aurate is then reduced to metallic gold using any of the techniques described previously for the reduction of palladium and copper from the fixed palladium and copper compounds on the surface of the support. Such reduction of potassium aurate is carried out without any necessity for the intermediate steps of fixing the gold on the support as a water-insoluble compound and washing such compound until chlorine-free, as described previously for palladium and as ordinarily required for gold in the preparation of vinyl acetate catalysts comprising palladium and gold. The elimination of such fixing and washing steps in connection with gold is an important advantage in the preparation of the catalyst of this invention.

One of the problems in producing VA catalysts has been low noble metal retention on the catalyst support. The use of $KAuO_2$ precursors offer a method to produce salt free highly dispersed metallic particles with no fixing step involved for the Au complexes. An advantage of no fixing step for the Au complexes is the increased gold retention since Au is partially washed out of the catalyst during fixing/washing step under prior art techniques. A high gold metal retention catalyst can be obtained by this method. The catalyst also contains Cu, Pd and Au distributed in a thin shell at or near the surface of the catalyst support.

Although the catalysts of this invention have been described primarily in connection with those containing only palladium, gold and copper as catalytically active metals, the catalyst may also contain one or more additional catalytically active metallic elements in the form of the free metal, oxide, or mixture of free metal and oxide. Such metallic elements may be, for example, magnesium, calcium, barium, zirconium and/or cerium. When a metal in addition to palladium, gold and copper is desired in the catalyst, the support may usually be impregnated with a water soluble salt of such metal dissolved in the same impregnating solution as that containing the water-soluble palladium and copper salts. The support may thus be simultaneously impregnated with water-soluble salts of palladium, copper and the additional metal which are then simultaneously fixed and reduced in the same manner as described previously for palladium and copper without any additional metal. The catalyst containing the palladium and copper as the free metal and an additional metal as the oxide and/or free metal is then impregnated with potassium aurate which is subsequently reduced to gold as free metal without an intermediate fixing step as described previously in connection with palladium and copper as the only other metals in addition to gold.

Advantageously, the catalyst containing palladium, gold and copper in free metallic form may optionally be impregnated with a solution of an alkali metal acetate, preferably potassium or sodium acetate, and most preferably potassium acetate (KOAc). After drying, the finished catalyst may contain, for example, about 10 to about 70, preferably about 20 to about 60 grams of alkali metal acetate per liter of finished catalyst.

Optionally, $KAuO_2$ may be added together with KOAc in one step to the prereduced Pd/Cu catalyst.

When vinyl acetate is prepared using the catalyst of the present invention, a stream of gas, which contains ethylene, oxygen or air, acetic acid, and desirably an alkali metal acetate, is passed over the catalyst. The composition of the gas stream can be varied within wide limits, taking in account explosive limits. For example, the molar ratio of ethylene to oxygen can be about 80:20 to about 98:2, the molar ratio of acetic acid to ethylene can be about 100:1 to about 1:100, preferably about 10:1 to 1:10, and most preferably about 1:1 to about 1:8, and the content of gaseous alkali metal acetate can be about 1 to about 100 ppm based on the weight of acetic acid employed. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be a somewhat reduced pressure, normal pressure or elevated pressure, preferably a pressure of up to about 20 atmospheres gauge.

The following examples further illustrates the invention.

EXAMPLES 1 to 12

These examples illustrate the preparation of catalysts under this invention containing varying amounts of palladium and gold in free metallic form.

A support material containing prereduced palladium metal was prepared as follows: The support material in an amount of 250 ml consisting of Sud Chemie KA-160 silica spheres having a nominal diameter of 7 mm., a density of about 0.562 g/ml, in absorptivity of about 0.583 g $H_2O$/g support, a surface area of about 160 to 175 $m^2$/g, and a pore volume of about 0.68 ml/g., was first impregnated by incipient wetness with 82.5 ml of an aqueous solution of sodium tetrachloropalladium (II) ($Na_2PdCl_4$) and cupric chloride ($CuCl_2$) sufficient to provide about 7 grams of elemental palladium and about 1.9 grams of elemental copper per liter of catalyst. The support was shaken in the solution for 5 minutes to ensure complete absorption of the solution. The palladium and copper were then fixed to the support as palladium(II) and cupric hydroxides by contacting the treated support by roto-immersion for 2.5 hours at approximately 5 rpm with 283 ml of an aqueous sodium hydroxide solution prepared from 50% w/w NaOH/$H_2O$ in an amount of 120% of that needed to convert the palladium and copper to their hydroxides. The solution was drained from the treated support which was then washed with deionized water until chloride free (about 5 hours) and dried overnight at 150° C. under constant nitrogen purge. The palladium and copper were then reduced to the free metal by contacting the support with ethylene (5% in nitrogen) in the vapor phase at 150° C. for 5 hours, or with, hydrazine at room temperature for 4 hours followed by washing with deionized water for 2 hours and drying in an oven at 150° C. for 5 hours, to obtain a support containing nominal amounts of 7 grams/liter of prereduced Pd and 1.9 grams/liter of prereduced copper.

In the production of potassium aurate utilized to impregnate the support with gold, auric hydroxide, $Au(OH)_3$, was first prepared by mixing 300 g of sodium tetrachlorogold (III), $NaAuCl_4$, containing 0.20 g Au/g solution with 73.6 g of a 50% w/w NaOH/$H_2O$ dissolved in 200 ml deionized water. An excess of NaOH was added to bring the pH to about 8 and the solution was stirred and heated to 60° C. for 3 hours to form an orange precipitate Filtration yielded on orange solid which was washed with deionized water until chloride free and dried in a vacuum oven at 50° C. in a flow of $N_2$ to obtain an orange red solid of $Au(OH)_3$. Analysis of the solid indicated a gold content of 79.5 wt. % which agrees with the calculated value.

Auric hydroxide in an amount of 0.5 gram was mixed with 0.12 gram of KOH in 35 ml of water, and the resulting orange suspension was heated to a temperature of 82 to 85° C. and stirred at this temperature until all solids were dissolved to yield a clear yellow solution of potassium aurate, $KAuO_2$, in an amount containing about 0.4 gram of elemental gold. This solution was added to 100 ml of support containing nominal amounts of 7 grams/liter of prereduced Pd and 1.9 grams/liter of prereduced Cu prepared as described previously using ethylene as reducing agent. The impregnation was conducted for about 25–30 min. The catalyst was dried in an oven at 100° C. for 5 hours in a flow of $N_2$ purge. The gold in the treated catalyst was then reduced by 5% ethylene in $N_2$ at 120° C. for 5 hours to obtain free metallic gold on the support.

Finally the catalyst was impregnated by incipient wetness with an aqueous solution of 4 g of potassium acetate in 33 ml $H_2O$ and dried in a fluid bed drier at 100° C. for 1 hour.

The foregoing description of the preparation of a catalyst in accordance with this invention is specific to the catalysts of Examples 1 to 3 which contain nominal amounts, i.e., corresponding to the concentrations and amounts of the impregnating solutions, of 7 grams of Pd, 1.9 grams of Cu, and 4 grams of Au per liter of catalyst, and in which the Pd, Cu and Au are all reduced with ethylene. In Example 4, the procedures of Examples 1–3 were followed except that the amounts of materials and reagents were increased proportionately so as to obtain a batch of 6 liters of catalyst containing the same nominal amounts of copper, palladium and gold as the catalyst of Examples 1–3. The catalysts of Examples 5 to 12 which may contain amounts of Pd, Cu and/or Au different from those of Examples 1–3, are similarly prepared except that the concentration of the $Na_2PdCl_4$, $CuCl_2$ and/or $KAuO_2$ in the appropriate impregnating solution is changed to obtain the desired nominal amounts of Pd, Au and/or Cu on the support, and the reduction of Pd, Cu and Au is each accomplished with either ethylene or hydrazine, as previously described. The reducing agent (Red.) used in the preparation ($C_2H_4$ or $N_2H_4$), the nominal amounts of Pd, Cu and Au corresponding to the concentrations and amounts of impregnating solutions (Nom. Amt., g/l), and actual amounts of Pd, Cu and Au on the catalysts of Examples 1–12 determined by analysis, in terms of percentage of total catalyst including the support (% of Tot. Cat.) and percentages of nominal amounts (% of Nom. Amt.), are shown in Table I.

The catalysts of the examples were tested for their activity and selectivity to various by-products in the production of vinyl acetate by reaction of ethylene, oxygen and acetic acid. To accomplish this, about 60 ml of the catalyst prepared as described were placed in a stainless steel basket with the temperature capable of being measured by a thermocouple at both the top and bottom of the basket. The basket was placed in a Berty continuously stirred tank reactor of the recirculating type and was maintained at a temperature which provided about 45% oxygen conversion with an electric heating mantle. A gas mixture of about 50 normal liters (measured at N.T.P.) of ethylene, about 10 normal liters of oxygen, about 49 normal liters of nitrogen, about 50 g of acetic acid, and about 4 mg of potassium acetate, was caused to travel under pressure at about 12 atmospheres through the basket, and the catalyst was aged under these reaction conditions for at least 16 hours prior to a two hour run, after which the reaction was terminated. Analysis of the products was accomplished by on-line gas chromatographic analysis combined with off-line liquid product analysis by condensing the product stream at about 10° C. to obtain optimum analysis of the end products carbon dioxide ($CO_2$), heavy ends (HE) and ethyl acetate (ETOAc), the results of which were used to calculate the selectivities of these materials for each example (Ex.) as shown in Table I. The relative activity of the reaction expressed as an activity factor (Act.) is also shown in Table I and is computer calculated in the following way: The computer program uses a series of equations that correlates the activity factor with the catalyst temperature (during the reaction), oxygen conversion, and a series of kinetic parameters for the reactions that take place during VA synthesis. More generally, the activity factor is inversely related to the temperature required to achieve constant oxygen conversion.

EXAMPLE 13

Preparation of VA Catalyst by Impregnation of (1) $KAuO_2$ Followed by (2) Pd or Pd/Cu Preparation of VA catalyst by impregnation of (1) KAuO2 followed by (2) Pd/Cu. The support material in an amount of 100 ml consisting of Sud Chemie KA-160 silica spheres having a nominal diameter of 7 mm, a density of about 0.562 g/ml, in absorptivity of about 0.583 g $H_2O$/g support, a surface area of about 160 to 175 m2/g, and a pore volume of about 0.68 ml/g, was first impregnated by incipient wetness with 35 ml aqueous solution of $KAuO_2$ (prepared as example 1 to 12) sufficient to provide about 4 grams of elemental gold per liter of catalyst. The support was shaken in the solution for 5 minutes to ensure complete absorption of the solution. The treated support was placed in an oven and was dried 5 hours at 100° C. under constant $N_2$ purge. The reduction was carried out with 5% $C_2H_4$ in $N_2$ at 120° C. for 5 hours. To this prereduced gold catalyst, was then impregnated by incipient wetness with 35 ml of aqueous solution of sodium tetrachloropalladium (II) ($Na_2PdCl_4$) and cupric chloride ($CuCl_2$) sufficient to provide about 7 grams of elemental palladium and about 1.9 grams of elemental copper per liter of catalyst. The support was shaken in the solution for 5 minutes to ensure complete absorption of the solution. The palladium and copper were then fixed to the support as palladium(II) and cupric hydroxides by contacting the treated support by roto-immersion for 2.5 hours at approximately 5 rpm with 120 ml of an aqueous sodium hydroxide solution prepared from 50% w/w $NaOH/H_2O$ in an amount of 120% of that needed to convert the palladium and copper to their hydroxides. The solution was drained from the treated support which was then washed with deionized water until chloride free (about 5 hours) and dried

TABLE I

| | | Metal Content of Catalyst | | | | | | | | | | | |
|---|---|---|---|---|---|---|---|---|---|---|---|---|---|
| | | Nom. Amt. g/l | | | Act. Amt (analysis) g/l | | | % Metal Retention | | | | Selectivity % | |
| Ex. | Red. | Pd | Au | Cu | Pd | Au | Cu | Pd | Au | Cu | Act. | $CO_2$ | HE | EtOAc |
| 1 | $C_2H_4$ | 7 | 4 | 1.9 | 6.65 | 3.88 | 1.71 | 95 | 97 | 90 | 1.87 | 7.40 | 1.126 | 0.049 |
| 2 | $C_2H_4$ | 7 | 4 | 1.9 | 6.44 | 3.80 | 1.9 | 92 | 95 | 100 | 1.74 | 7.32 | 0.871 | 0.04 |
| 3 | $C_2H_4$ | 7 | 4 | 1.9 | 6.58 | 3.64 | 1.60 | 94 | 91 | 84 | 1.87 | 7.68 | 1.024 | 0.031 |
| 4 | $C_2H_4$ | 7 | 4 | 1.9 | 6.30 | 3.72 | 1.9 | 90 | 93 | 100 | 1.71 | 7.45 | 0.948 | 0.108 |
| 5 | $N_2H_4$ | 7 | 4 | 1.9 | 5.95 | 3.88 | 1.84 | 85 | 97 | 97 | 1.99 | 9.10 | 0.754 | 0.106 |
| 6 | $C_2H_4$ | 7 | 5 | 1.9 | 6.65 | 4.50 | 1.84 | 95 | 90 | 97 | 1.87 | 7.14 | 1.128 | 0.044 |
| 7 | $N_2H_4$ | 7 | 5 | 1.9 | 6.51 | 4.80 | 1.84 | 93 | 96 | 97 | 1.98 | 9.12 | 0.906 | 0.114 |
| 8 | $C_2H_4$ | 7 | 3.4 | 1.9 | 6.65 | 3.13 | 1.84 | 95 | 92 | 97 | 1.88 | 7.44 | 1.280 | 0.050 |
| 9 | $C_2H_4$ | 7 | 4 | 1 | 6.09 | 3.28 | 0.94 | 87 | 82 | 94 | 2.13 | 8.16 | 1.552 | 0.064 |
| 10 | $C_2H_4$ | 8 | 4.57 | 1.9 | 7.60 | 4.43 | 1.79 | 95 | 97 | 94 | 2.11 | 8.2 | 1.595 | 0.046 |
| 11 | $N_2H_4$ | 8 | 4.57 | 1.9 | 7.36 | 4.34 | 1.79 | 92 | 95 | 94 | 2.29 | 9.43 | 1.151 | 0.107 |
| 12 | $C_2H_4$ | 8 | 4.57 | 2.2 | 7.76 | 4.39 | 2.2 | 97 | 96 | 100 | 1.83 | 7.59 | 1.036 | 0.038 |

The values shown in Table I indicate that the catalysts of this invention in many instances can be used to synthesize vinyl acetate by reaction of ethylene, oxygen, and acetic acid with lower $CO_2$ and heavy ends selectivities than various conventional and/or commercial catalysts comprising palladium and gold, while maintaining satisfactory levels of activity. Following is my revised vision for this part:

overnight at 150° C. under constant nitrogen purge. The palladium and copper were then reduced to the free metal by contacting the support with ethylene (5% in nitrogen) in the vapor phase at 150° C. for 5 hours, or with, hydrazine at room temperature for 4 hours followed by washing with deionized water for 2 hours and drying in an oven at 150° C. for 5 hours, to obtain a catalyst containing nominal amounts of 4 g/liter of Au, 7 grams/liter of Pd and 1.9 grams/liter of Cu. This catalyst was then impregnated with 4 g of KOAc in 33 ml H$_2$O and dried in fluid bed dryer at 100° C. for 1.5 hours.

| Pd/Au/Cu catalyst performance: | CO$_2$ | 8.80 |
| --- | --- | --- |
| | Activity: | 1.87 |
| | HE | 0.702 |
| | EtOAc | 0.078 |

What is claimed is:

1. A catalyst for the production of vinyl acetate by reaction of ethylene, oxygen and acetic acid comprising a porous support on the porous surfaces of which is deposited catalytically effective amounts of metallic palladium, gold, and copper, said catalyst having been prepared by steps comprising impregnating said porous support, the porous surfaces of which contain catalytically effective amounts of prereduced metallic palladium and copper, with a solution of potassium aurate, and reducing the potassium aurate to a catalytically effective amount of metallic gold.

2. The catalyst of claim 1 wherein said support containing prereduced palladium and copper is prepared by steps comprising impregnating said support with an aqueous solution of water-soluble palladium and copper salts, fixing said palladium and copper as water-insoluble compounds by reaction with an appropriate alkaline compound, and reducing to their free metallic state the water-insoluble compounds of palladium and copper present on the support.

3. The catalyst of claim 2 wherein said water-soluble palladium salt is sodium tetrachloropalladium(II), and said water-soluble copper salt is cupric chloride.

4. The catalyst of claim 1 containing about 1 to about 10 grams of palladium, about 0.5 to about 10 grams of gold, and about 0.3 to about 5.0 grams of copper per liter of catalyst, with the amount of gold being from about 10 to about 125 wt. % based on the weight of palladium.

5. The catalyst of claim 1 also containing a deposit of an alkali metal acetate.

6. The catalyst of claim 5 wherein said alkali metal acetate is potassium acetate which is present in an amount of about 10 to about 70 grams/liter of catalyst.

7. The catalyst of claim 1 wherein the support is (1) contacted with a solution of potassium aurate, and reducing the potassium aurate to a catalytically effective amount of metallic gold, (2) contacting the gold supported catalyst with water soluble palladium and copper complexes, (3) fixing and reducing the palladium and copper complexes to their metallic state.

8. The catalyst of claim 7 wherein the catalyst is prepared with sodium free reagents.

9. The catalyst of claim 7 wherein the catalyst forms a thin shell of Pd, Au and Cu on the surface of the support.

10. The catalyst of claim 7 also containing a deposit of an alkali metal acetate.

11. The catalyst of claim 1 wherein the catalyst is prepared with sodium free reagents.

12. The catalyst of claim 1 wherein potassium aurate is added simultaneously with potassium acetate.

13. A method of preparing a catalyst for the production of vinyl acetate by reaction of ethylene, oxygen and acetic acid comprising impregnating a porous support, the porous surfaces of which contain catalytically effective amounts of prereduced palladium and copper, with a solution of potassium aurate, and reducing the potassium aurate to a catalytically effective amount of metallic gold.

14. The method of claim 13 wherein said support containing prereduced palladium and copper is prepared by steps comprising impregnating said support with an aqueous solution of a water-soluble palladium and copper salts, fixing said palladium and copper as water-insoluble compounds by reaction with an appropriate alkaline compound, and reducing to their free metallic state the water-insoluble compounds of palladium and copper present on the support.

15. The method of claim 14 wherein said water-soluble palladium salt is sodium tetrachloropalladium(II) and said water soluble copper salt is cupric chloride.

16. The method of claim 13 wherein said porous support contains about 1 to about 10 grams of palladium, about 0.5 to about 10 grams of gold, and about 0.3 to about 5.0 grams of copper per liter of catalyst, with the amount of gold being from about 10 to about 125 wt. % based on the weight of palladium.

17. The method of claim 13 wherein said catalyst is impregnated with a solution of an alkali metal acetate.

18. The method of claim 17 wherein said alkali metal acetate is potassium acetate which is deposited on the catalyst in an amount of about 10 to about 70 grams/liter of catalyst.

19. The method of claim 17 wherein potassium aurate is added simultaneously with potassium acetate.

20. The method of claim 13 wherein the catalyst is prepared with sodium free reagents.

21. The method of claim 13 wherein the support is (1) contacted with a solution of potassium aurate, and reducing the potassium aurate to a catalytically effective amount of metallic gold, (2) contacting the gold supported catalyst with water soluble palladium and copper complexes, (3) fixing and reducing the palladium and copper complexes to their metallic state.

22. The method of claim 21 wherein the catalyst is prepared with sodium-free reagents.

23. The method of claim 21 wherein the catalyst forms a thin shell of Pd, Au and Cu on the surface of the support.

24. The method of claim 21 also containing a deposit of an alkali metal acetate.

25. The method of claim 24 wherein potassium aurate is added simultaneously with potassium acetate.

26. The method of claim 13 wherein the catalyst forms a thin shell of Pd, Au and Cu on the surface of the support.

* * * * *